United States Patent
Kawata et al.

(10) Patent No.: US 11,543,543 B2
(45) Date of Patent: Jan. 3, 2023

(54) RADIATION DETECTOR AND RADIATION DIAGNOSIS APPARATUS

(71) Applicant: CANON MEDICAL SYSTEMS CORPORATION, Otawara (JP)

(72) Inventors: Go Kawata, Nagareyama (JP); Hiroaki Nakai, Nasushiobara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 0 days.

(21) Appl. No.: 17/355,777

(22) Filed: Jun. 23, 2021

(65) Prior Publication Data
US 2022/0003886 A1    Jan. 6, 2022

(30) Foreign Application Priority Data
Jul. 3, 2020 (JP) .............................. JP2020-115308

(51) Int. Cl.
*G01T 1/24* (2006.01)
*G01T 1/17* (2006.01)

(52) U.S. Cl.
CPC ............... *G01T 1/241* (2013.01); *G01T 1/17* (2013.01); *G01T 1/247* (2013.01)

(58) Field of Classification Search
CPC ............ G01T 1/17; G01T 1/241; G01T 1/247
See application file for complete search history.

(56) References Cited

U.S. PATENT DOCUMENTS

| | | | | |
|---|---|---|---|---|
| 5,719,401 A * | 2/1998 | Chaney | ............... | G01T 1/2928 250/214 VT |
| 10,444,381 B2 | 10/2019 | Steadman Booker et al. | | |
| 2007/0280409 A1 * | 12/2007 | Konno | .................. | G01T 1/249 378/19 |
| 2007/0290142 A1 | 12/2007 | Du et al. | | |
| 2008/0049892 A1 * | 2/2008 | Maltz | ..................... | G21K 5/04 378/65 |
| 2008/0175347 A1 * | 7/2008 | Tkaczyk | ................. | G01T 1/24 378/7 |
| 2011/0019795 A1 * | 1/2011 | Fujita | ..................... | G01T 1/247 378/19 |
| 2012/0269321 A1 * | 10/2012 | Behling | ................ | H01J 35/24 378/138 |
| 2015/0092918 A1 * | 4/2015 | Crocco | .................. | G01N 23/04 250/370.15 |
| 2018/0356541 A1 * | 12/2018 | Steadman Booker | .. | G01T 1/249 |

FOREIGN PATENT DOCUMENTS

JP 2018-013338 A 1/2018

* cited by examiner

*Primary Examiner* — Blake C Riddick
(74) *Attorney, Agent, or Firm* — Oblon, McClelland, Maier & Neustadt, L.L.P.

(57) ABSTRACT

A radiation detector according to an embodiment includes: a cathode electrode, a plurality of anode electrodes, a crystal, an anti-scatter grid, and a conductive part. The cathode electrode is provided on the radiation incident side. The plurality of anode electrodes are arranged so as to oppose the cathode electrode. The crystal is provided between the cathode electrode and the plurality of anode electrodes and configured to convert incident radiation into electrons. The conductive part is provided between the plurality of anode electrodes and has a conductivity higher than that of the crystal. The anti-scatter grid is provided on the radiation incident side of the cathode electrode so as to oppose the conductive part via the crystal, while being arranged in a first direction.

8 Claims, 6 Drawing Sheets

RADIATION DETECTOR AND RADIATION DIAGNOSIS APPARATUS

CROSS-REFERENCE TO RELATED APPLICATIONS

This application is based upon and claims the benefit of priority from Japanese Patent Application No. 2020-115308, filed on Jul. 3, 2020; the entire contents of which are incorporated herein by reference.

FIELD

Embodiments described herein relate generally to a radiation detector and a radiation diagnosis apparatus.

BACKGROUND

In a radiation detector of an X-ray computed tomography apparatus or the like, a collimator (an Anti-Scatter Grid, hereinafter, "ASG") may be arranged on the side where radiation becomes incident to the radiation detector (hereinafter, "radiation incident side"). The ASG is configured to inhibit detection of the radiation that becomes incident at boundaries of a plurality of detecting elements included in the radiation detector.

However, when the radiation detector is of a direct-conversion type that directly detects the incident radiation, a part of electric charges occurring inside the radiation detector may also be detected, in some situations, by another detecting element positioned adjacent to the detecting element corresponding to the radiation incident position. This phenomenon is called charge sharing (hereinafter, "CS") and can be a cause of crosstalk and may bring about undesirable problems such as occurrence of noise, for example. To reduce the CS between ASGs, the ASGs need to have sufficient blocking capabilities, and the intervals between pixels need to be approximately equal to the width of each of the ASGs. When the ASGs are designed to realize high definition in conjunction with miniaturization of the detecting elements, the intervals between the pixels required to reduce the CS may lower radiation detection efficiency and may lead to an increase in unnecessary radiation exposure of the examined subject.

DETAILED DESCRIPTION

Exemplary embodiments of a radiation diagnosis apparatus and a radiation detector included in the radiation diagnosis apparatus will be explained in detail below, with reference to the accompanying drawings. In the embodiments described below, some of the constituent elements having mutually the same reference characters are assumed to perform mutually the same operations, and the duplicate explanations thereof will be omitted as appropriate. To explain specific examples, the radiation diagnosis apparatus according to the present embodiments is assumed to be an X-ray Computed Tomography apparatus (hereinafter, "X-ray CT apparatus"). In this situation, the radiation detector included in the radiation diagnosis apparatus corresponds to an X-ray detector, whereas the radiation corresponds to X-rays. However, the radiation diagnosis apparatus does not necessarily have to be an X-ray CT apparatus and may be a nuclear medicine diagnosis apparatus or an X-ray diagnosis apparatus. When the radiation diagnosis apparatus is a nuclear medicine diagnosis apparatus, the radiation detector corresponds to a gamma-ray detector, for example.

The radiation detector described in the embodiments below includes a cathode electrode, a plurality of anode electrodes, a crystal, an electrically-conductive part (hereinafter, "conductive part"), and an anti-scatter grid. The cathode electrode is provided on the radiation incident side. The plurality of anode electrodes are arranged so as to oppose the cathode electrode. The crystal is provided between the cathode electrode and the plurality of anode electrodes and is configured to convert incident radiation into electrons. The conductive part is provided between the plurality of anode electrodes and has a higher conductivity than that of the crystal. The anti-scatter grid is provided on the radiation incident side of the cathode electrode so as to oppose the conductive part via the crystal, while being arranged in a first direction.

The X-ray CT apparatus described in the embodiments below is an apparatus capable of carrying out photon counting CT. In other words, the X-ray CT apparatus is an apparatus capable of reconstructing X-ray CT image data having a high Signal-to-Noise (SN) ratio, by counting X-rays that have passed through the examined subject while employing a detector that uses a photon counting scheme, instead of a conventional detector of an integration type (using a current mode measuring scheme). Further, the detector using the photon counting scheme according to the present embodiments is a detector of a direct-conversion type (hereinafter, "direct-conversion type detector") including the crystal configured to convert the incident X-rays into the electrons, i.e., electric signals. In other words, the radiation detector included in the radiation diagnosis apparatus corresponds to the direct-conversion type detector including the crystal configured to directly convert the radiation that has become incident to the radiation detector, into the electrical signals.

Embodiments

Figure 1:
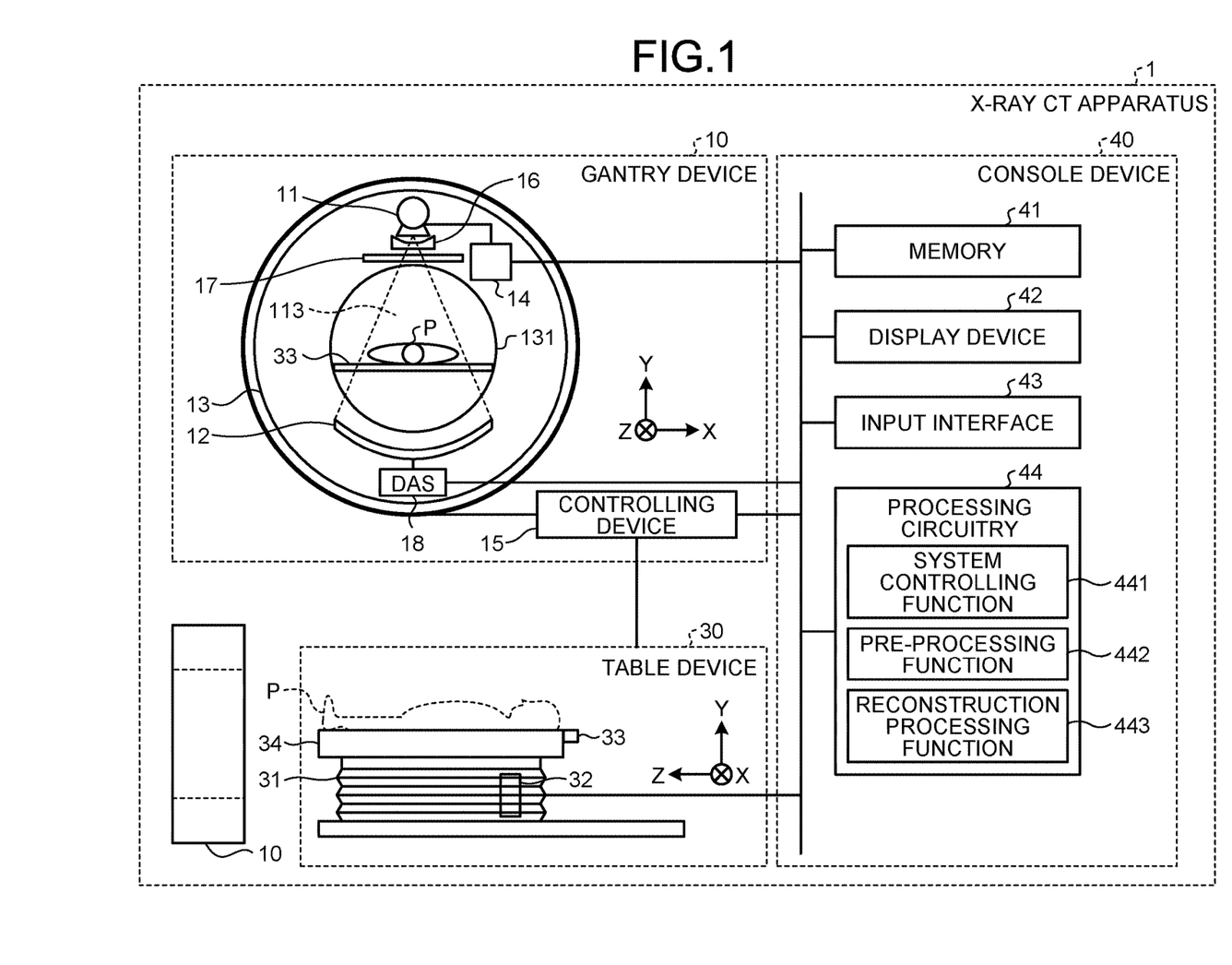
FIG. 1 is a diagram illustrating an exemplary configuration of an X-ray Computed Tomography (CT) apparatus according to an embodiment.

FIG. 1 is a diagram illustrating an exemplary configuration of an X-ray CT apparatus 1 according to an embodiment of the present disclosure. As illustrated in FIG. 1, the X-ray CT apparatus 1 includes a gantry device 10, a table device 30, and a console device 40. In the present embodiment, the rotation axis of a rotating frame 13 in a non-tilted state or the longitudinal direction of a tabletop 33 of the table device 30 is defined as a Z-axis direction, whereas an axial direction orthogonal to the Z-axis direction and parallel to the floor surface is defined as an X-axis direction, and an axial direction orthogonal to the Z-axis direction and perpendicular to the floor surface is defined as a Y-axis direction. Although FIG. 1 depicts the gantry device 10 in multiple locations for the sake of convenience in the explanation, the actual X-ray CT apparatus 1 is configured to include one gantry device 10.

The gantry device 10 and the table device 30 are configured to operate on the basis of operations received from the user via the console device 40 or operations received from the user via an operating unit provided for the gantry device 10 or the table device 30. The gantry device 10, the table device 30, and the console device 40 are connected in a wired or wireless manner so as to be able to communicate with one another.

The gantry device 10 is a device including an imaging system configured to radiate X-rays onto an examined subject (hereinafter, "patient") P and to acquire projection data from detection data of X-rays that have passed through the patient P. The gantry device 10 includes an X-ray tube 11 (an X-ray generating unit), a direct-conversion type detector 12, the rotating frame 13, an X-ray high-voltage device 14, a controlling device 15, a wedge 16, a collimator 17, and a Data Acquisition System (DAS) 18.

The X-ray tube 11 is a vacuum tube configured to generate X-rays by emitting thermo electrons from a negative pole (a filament) toward a positive pole (a target), with application of high voltage and supply of a filament current from the X-ray high-voltage device 14. As a result of the thermo electrons colliding with the target, X-rays are generated. The X-rays occurring at an X-ray tube focal point of the X-ray tube 11 are formed to have a cone-beam shape via the collimator 17, for example, before being radiated onto the patient P. Examples of the X-ray tube 11 include a rotating anode X-ray tube configured to generate the X-rays by emitting the thermo electrons onto a rotating anode (positive pole).

The direct-conversion type detector 12 is configured to detect, in units of photons, the X-rays that were radiated from the X-ray tube 11 and have passed through the patient P and configured to output an electrical signal corresponding to the amount of the X-rays to the DAS 18. For example, the direct-conversion type detector 12 includes a plurality of rows of detecting elements in each of which a plurality of detecting elements are arranged along a slice direction (a row direction) parallel to the Z direction. The plurality of rows of detecting elements are arranged in a channel direction along an arc while being centered on the focal point of the X-ray tube 11. In addition, the direct-conversion type detector 12 further includes a scattered ray eliminating unit arranged along at least the channel direction, on the front face of the plurality of rows of detecting elements that is positioned on the X-ray incident side.

Every time an X-ray photon becomes incident thereto, each of the plurality of detecting elements is configured to output an electrical signal (an analog signal) corresponding to one pulse. By counting the quantity of the electrical signals (the pulses), it is possible to count the quantity of the X-ray photons that have become incident to each of the detecting elements. Further, by performing various types of calculating processes on the signals, it is possible to measure an energy value of the X-ray photons that caused the output of the signals.

For example, in each of the plurality of detecting elements, an electrode is provided on the face opposing a crystal (which may be called a semiconductor crystal) of cadmium telluride (CdTe) or cadmium zinc telluride (CdZnTe), so that an electric field is generated by application of bias voltage. In the direct-conversion type detector 12, when the radiation is absorbed by the crystal, an electron-hole pair is generated, and the signal is output as a result of electrons moving to the anode side (the side of the anode electrodes (pixel electrodes)), and the electron holes moving to the cathode side (the side of the cathode electrode (the common electrode). Each of the plurality of detecting elements may include a plurality of pixel electrodes. A detailed configuration of the direct-conversion type detector 12 according to the present embodiment will be explained more specifically later.

In addition to the detecting elements, the direct-conversion type detector 12 includes a plurality of Application Specific Integrated Circuits (hereinafter, "ASICs") connected to the detecting elements and configured to count the X-ray photons detected by the detecting elements. The ASICs are configured to count the quantity of the X-ray photons that have become incident to the detecting elements, by discriminating individual electric charges output by the detecting elements. Further, by performing a calculating process based on the magnitude of each of the electric charges, the ASICs are configured to measure the energy of the counted X-ray photons. Further, the ASICs are configured to output the results of counting the X-ray photons to the DAS 18, as digital data.

The scattered ray eliminating unit is arranged on the X-ray incident side of the cathode electrode. The scattered ray eliminating unit has a plurality of scattered ray eliminating parts that are arranged along the first direction so as to oppose via the crystal, while being positioned between any two adjacently-positioned anode electrodes among the plurality of anode electrodes. In other words, the scattered ray eliminating unit is arranged in the first direction, so as to oppose the conductive part (explained later) having a higher conductivity than that of the crystal, while being provided between two anode electrodes. The first direction may be, for example, the channel direction orthogonal to the slice direction. In this situation, the scattered ray eliminating parts may each extend in the slice direction. Further, the scattered ray eliminating unit may further include a plurality of scattered ray eliminating parts arranged along a second direction different from the first direction. For example, the second direction may be the slice direction. In this situation, the scattered ray eliminating parts each may further extend in the channel direction. The scattered ray eliminating parts are, for example, configured by using X-ray blocking plates having a function of absorbing scattered X-rays and may be referred to as anti-scatter grid (hereinafter, "ASGs"). The ASGs may be called a one-dimensional collimator or a two-dimensional collimator depending on the dimension of the arranged formation.

In an example, the direct-conversion type detector 12 may have a structure in which an X-ray detecting module corresponding to a radiation detecting module is arranged along the channel direction. In this situation, the X-ray detecting module includes a detecting unit in which a plurality of rows of detecting elements are arranged along the channel direction, a scattered ray eliminating unit arranged on the X-ray incident side of the detecting unit, and a plurality of ASICs electrically connected to the plurality of detecting elements in the rows of detecting elements.

The rotating frame 13 is configured to support the X-ray tube 11 and the direct-conversion type detector 12 so as to be rotatable on the rotation axis. More specifically, the rotating frame 13 is an annular frame configured to support the X-ray tube 11 and the direct-conversion type detector 12 so as to oppose each other and configured to rotate the X-ray tube 11 and the direct-conversion type detector 12 via the controlling device 15 (explained later). The rotating frame 13 is rotatably supported on a fixed frame formed by using metal such as aluminum. More specifically, the rotating frame 13 is connected to an edge part of the fixed frame via a bearing. The rotating frame 13 is configured to rotate on a rotation axis Z with a constant angular speed, by receiving motive power from a driving mechanism of the controlling device 15.

In addition to the X-ray tube 11 and the direct-conversion type detector 12, the rotating frame 13 further includes and supports the X-ray high voltage device 14 and the DAS 18. The rotating frame 13 structured in this manner is housed in a casing that has a substantially circular cylindrical shape and has an opening (a bore) 131 formed therein, which serves as an imaging space. The opening 131 substantially coincides with a Field Of View (FOV). The central axis of the opening 131 coincides with the rotation axis Z of the rotating frame 13. For example, the detection data generated by the DAS 18 is transmitted from a transmitter including a Light Emitting Diode (LED) to a receiver including a photodiode and being provided in a non-rotation part (e.g., the fixed frame) of the gantry device 10, through optical communication, and is further transferred to the console device 40. In this situation, the method for transmitting the detection data from the rotating frame 13 to the non-rotation part of the gantry device 10 is not limited to the abovementioned optical communication and may be realized with any other contactless data transfer method.

The X-ray high-voltage device 14 includes: a high-voltage generating device including electrical circuits such as a transformer, a rectifier, and the like and having a function of generating the high voltage to be applied to the X-ray tube 11 and the filament current to be supplied to the X-ray tube 11; and an X-ray controlling device configured to control the output voltage in accordance with the X-rays radiated by the X-ray tube 11. The high-voltage generating device may be of a transformer type or of an inverter type. Further, the X-ray high-voltage device 14 may be provided on the rotating frame 13 or may be provided so as to belong to the fixed frame (not illustrated) of the gantry device 10.

The controlling device 15 includes: a processing circuitry having a Central Processing Unit (CPU) or the like; and the driving mechanism configured with a motor and an actuator, or the like. As hardware resources, the processing circuitry includes: a processor such as a CPU or a Micro Processing Unit (MPU); and a memory such as a Read-Only Memory (ROM) and/or a Random Access Memory (RAM). Further, the controlling device 15 may be realized by using an ASIC, a Field Programmable Gate Array (FPGA), or any of other types of Complex Programmable Logic Devices (CPLDs) and Simple Programmable Logic Devices (SPLDs). According to a command from the console device 40, the controlling device 15 is configured to control the X-ray high-voltage device 14, the DAS 18, and the like. The processor is configured to realize the abovementioned control by reading and carrying out the programs saved in the memory.

Further, the controlling device 15 has a function of receiving input signals from an input interface attached to either the console device 40 or the gantry device 10 and thus controlling operations of the gantry device 10 and the table device 30. For example, the controlling device 15 is configured to exercise control, upon receipt of the input signals, to cause the rotating frame 13 to rotate, to cause the gantry device 10 to tilt, and to bring the table device 30 and the tabletop 33 into operation. In this situation, the control to tilt the gantry device 10 may be realized as a result of the controlling device 15 rotating the rotating frame 13 on an axis parallel to the X-axis direction, according to tilting angle (tilt angle) information input through an input interface attached to the gantry device 10. Further, the controlling device 15 may be provided for the gantry device 10 or for the console device 40. Further, instead of saving the programs in the memory, the controlling device 15 may be configured to directly incorporate the programs in the circuits of the one or more processors. In that situation, the one or more processors realize the abovementioned control by reading and executing the programs incorporated in the circuits thereof.

The wedge 16 is a filter for adjusting the X-ray amount of the X-rays radiated from the X-ray tube 11. More specifically, the wedge 16 is a filter configured to pass and attenuate the X-rays radiated from the X-ray tube 11, so that the X-rays radiated from the X-ray tube 11 onto the patient P have a predetermined distribution. For example, the wedge 16 may be a wedge filter or a bow-tie filter and is a filter obtained by processing aluminum so as to have a predetermined target angle and a predetermined thickness.

The collimator 17 is configured with lead plates or the like used for narrowing down the X-rays having passed through the wedge 16 into an X-ray radiation range and is configured to form a slit with a combination of the plurality of lead plates or the like.

The DAS 18 includes a plurality of counting circuits. Each of the plurality of counting circuit includes an amplifier configured to perform an amplifying process on the electrical signals output from the detecting elements of the direct-conversion type detector 12; and an Analog/Digital (A/D) converter configured to convert the amplified electrical signals into digital signals. The DAS 18 is configured to generate the detection data, which is a result of the counting process using the detection signal from the direct-conversion type detector 12. The result of the counting process is data in which the quantity of the X-ray photons is assigned to each energy bin. For example, the DAS 18 counts the photons (the X-ray photons) derived from the X-rays that were radiated from the X-ray tube 11 and have passed through the patient P so as to obtain the result of the counting process by discriminating the energy levels of the counted photons. The detection data generated by the DAS 18 is transferred to the console device 40. The detection data is a set of data including a channel number and a row number of the detector pixel at the source of the generation, a view number identifying an acquired view (which may be referred to as a projection angle), and a value indicating the radiation amount of the detected X-rays. As the view numbers, the sequential order (the times of acquisition) in which the views were acquired may be used. Alternatively, numbers (e.g., 1 to 1,000) expressing rotation angles of the X-ray tube 11 may be used. Each of the plurality of counting circuits in the DAS 18 is realized, for example, by using a group of circuits including circuit elements capable of generating the detection data.

The table device 30 is a device on which the patient P to be scanned is placed so that the patient P can be moved. The table device 30 includes a base 31, a table driving device 32, a tabletop 33, and a tabletop supporting frame 34. The base 31 is a casing configured to support the tabletop supporting frame 34 so as to be movable in vertical directions. The table driving device 32 is a motor or an actuator configured to move the tabletop 33 on which the patient is placed P in long-axis directions of the tabletop 33. Under control of the console device 40 or control of the controlling device 15, the table driving device 32 is configured to move the tabletop 33. The tabletop 33 provided on the top face of the tabletop supporting frame 34 is a board on which the patient P is placed. In addition to the tabletop 33, the table driving device 32 may move the tabletop supporting frame 34 in long-axis directions of the tabletop 33.

The console device 40 includes a memory 41 (a storage unit), a display device 42 (a display unit), an input interface 43 (an input unit), and a processing circuitry 44 (a processing unit). Data communication among the memory 41, the display device 42, the input interface 43, and the processing circuitry 44 is carried out via a bus.

The memory 41 is a storage device storing therein various types of information such as a Hard Disk Drive (HDD), a Solid State Drive (SSD), or an integrated circuit storage device. For example, the memory 41 is configured to store therein projection data and reconstruction image data. Instead of an HDD, an SSD, or the like, the memory 41 may be a portable storage medium such as a Compact Disc (CD), a Digital Versatile Disc (DVD), or a flash memory or may be a driving device configured to read and write various types of information from and to a semiconductor memory element such as a Random Access Memory (RAM). Further, the storage region of the memory 41 may be inside the X-ray CT apparatus 1 or may be inside an external storage device connected via a network. Further, the memory 41 has stored therein a control program according to the present embodiment.

The display device 42 is configured to display various types of information. For instance, the display device 42 is configured to output a medical image (a CT image) generated by the processing circuitry 44, a Graphical User Interface (GUI) used for receiving various types of operations from the operator, and the like. For example, as the display device 42, it is possible to use, as appropriate, a Liquid Crystal Display (LCD) device, a Cathode Ray Tube (CRT) display device, an Organic Electroluminescence Display (OELD) device, a plasma display device, or any of other arbitrary display devices. Further, the display device 42 may be provided for the gantry device 10. Also, the display device 42 may be of a desktop type or may be configured by using a tablet terminal or the like capable of wirelessly communicating with the main body of the console device 40.

The input interface 43 is configured to receive various types of input operations from the operator, to convert the received input operations into electrical signals, and to output the electrical signals to the processing circuitry 44. For example, the input interface 43 is configured to receive, from the operator, an acquisition condition used at the time of acquiring the projection data, a reconstruction condition used at the time of reconstructing a CT image, an image processing condition used at the time of generating a post-processing image from the CT image, and the like. As the input interface 43, for example, it is possible to use, as appropriate, a mouse, a keyboard, a trackball, a switch, a button, a joystick, a touchpad, a touch panel display device, and/or the like.

In the present embodiment, the input interface 43 does not necessarily have to include one or more physical operation component parts such as the mouse, the keyboard, the trackball, the switch, the button, the joystick, the touchpad, the touch panel display device, and/or the like. For instance, possible examples of the input interface 43 include an electrical signal processing circuit configured to receive an electrical signal corresponding to an input operation from an external input device provided separately from the device and to output the electrical signal to the processing circuitry 44. The input interface 43 is an example of an input unit. Further, the input interface 43 may be provided for the gantry device 10. Furthermore, the input interface 43 may be configured by using a tablet terminal or the like capable of wirelessly communicating with the main body of the console device 40.

The processing circuitry 44 is configured to control operations of the entirety of the X-ray CT apparatus 1, in accordance with the electrical signals corresponding to the input operations and being output from the input interface 43. As hardware resources, the processing circuitry 44: includes a processor such as a CPU, an MPU, or a Graphics Processing Unit (GPU); and a memory such as a ROM and/or a RAM. By employing the processor configured to execute programs loaded into the memory, the processing circuitry 44 is configured to execute a system controlling function 441 (a system controlling unit), a pre-processing function 442, and a reconstruction processing function 443 (a reconstructing unit). The functions 441 to 443 do not necessarily have to be realized by the single processing circuit. It is also acceptable to structure a processing circuit by combining together a plurality of independent processors, so that the functions 441 to 443 are realized as a result of the processors executing the programs.

On the basis of the input operations received from the operator via the input interface 43, the system controlling function 441 is configured to control the functions of the processing circuitry 44. More specifically, the system controlling function 441 is configured to read the control program stored in the memory 41, to load the read control program into the memory in the processing circuitry 44, and to control functional units of the X-ray CT apparatus 1 according to the loaded control program. For example, on the basis of the input operations received from the operator via the input interface 43, the processing circuitry 44 is configured to control the functions of the processing circuitry 44.

The pre-processing function 442 is configured to generate data by performing pre-processing processes such as a logarithmic conversion process, an offset correcting process, an inter-channel sensitivity correcting process, a beam hardening correction, and/or the like, on the detection data output from the DAS 18. The data before the pre-processing processes may be referred to as raw data, whereas the data after the pre-processing processes may be referred to as projection data.

The reconstruction processing function 443 is configured to generate the CT image data by performing a reconstructing process using a Filtered Back Projection (FBP) method, a successive approximation reconstruction method, or the like, on the projection data generated by the pre-processing function 442. The reconstruction processing function 443 is configured to store the reconstructed CT image data into the memory 41. The projection data generated from the counting result obtained in the photon counting CT includes information about energy of the X-rays attenuated by passing through the patient P. For this reason, for example, the reconstruction processing function 443 is capable of reconstructing X-ray CT image data of a specific energy component. Further, for example, the reconstruction processing function 443 is capable of reconstructing X-ray CT image data of each of a plurality of energy components.

Further, for example, the reconstruction processing function 443 is capable of generating image data in which a tone corresponding to an energy component is assigned to each of the pixels in the X-ray CT image data representing the energy components, so that a plurality of pieces of X-ray CT image data color-coded according to the energy components are superimposed on one another. Further, for example, the reconstruction processing function 443 is capable of generating image data that makes it possible to identify a substance by using a K-absorption edge unique to the substance. Other examples of image data generated by the reconstruction processing function 443 include monochrome X-ray image data, density image data, and effective atomic number image data. The processing circuitry 44 configured to realize the pre-processing function 442 and the reconstruction processing function 443 corresponds to the image generating unit configured to generate a medical image on the basis of the electrons output from the anode electrodes included in the direct-conversion type detector 12.

A configuration of the X-ray CT apparatus 1 according to the embodiment has thus been explained. In this configuration, the direct-conversion type detector 12 included in the X-ray CT apparatus 1 is configured to be able to inhibit crosstalk between the detecting elements positioned adjacent to each other.

Figure 2:
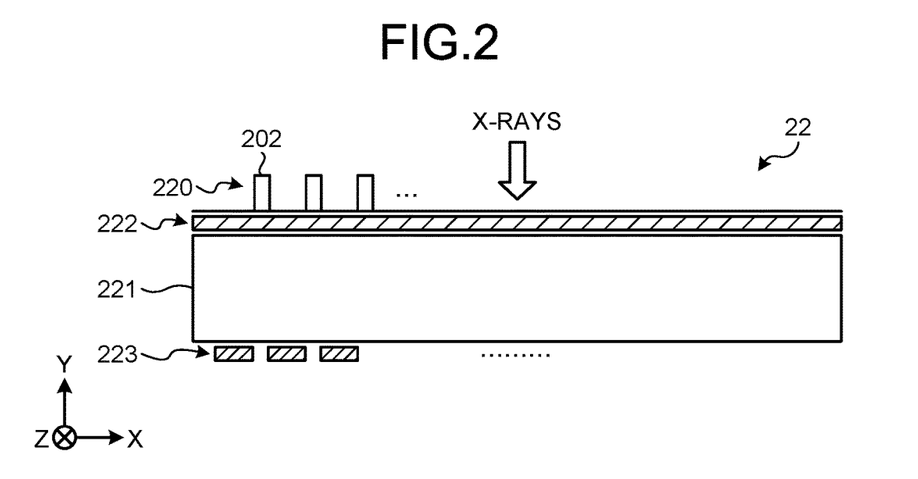
FIG. 2 is a drawing for explaining charge sharing according to the embodiment.
Figure 3:
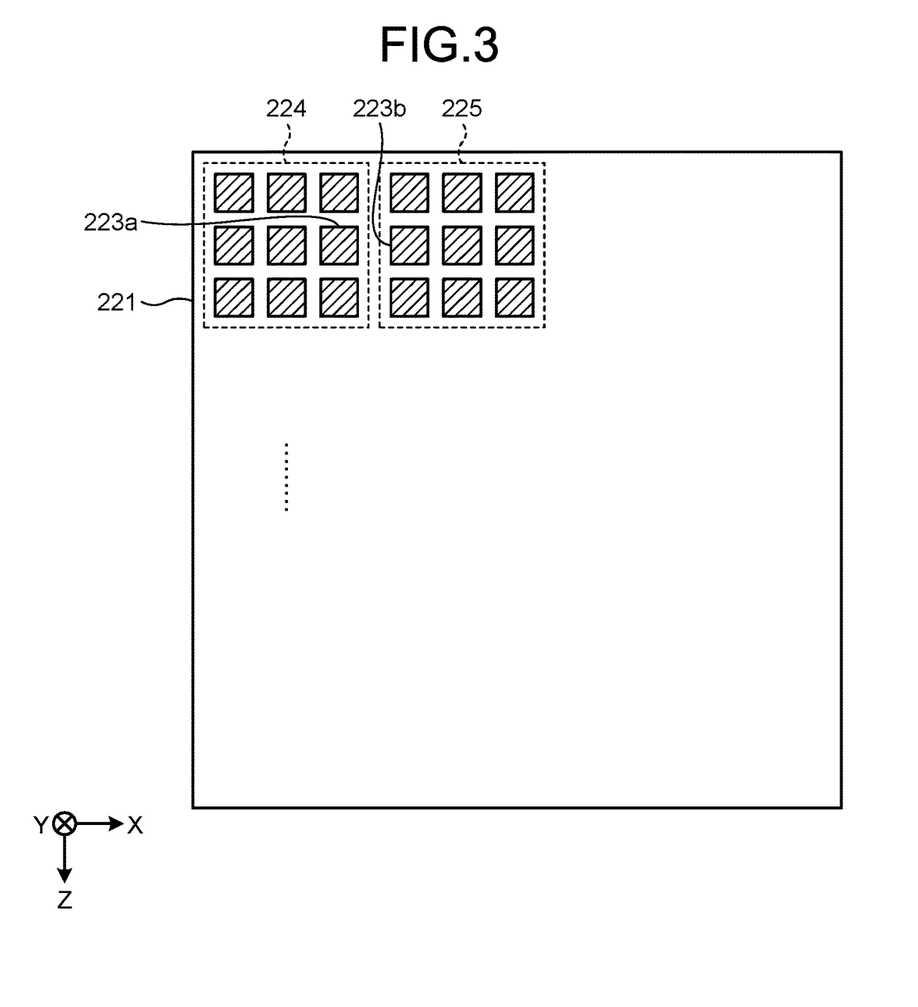
FIG. 3 is another drawing for explaining the charge sharing according to the embodiment.

Next, charge sharing, which can be a cause of crosstalk, will be explained, with reference to FIGS. 2 and 3. FIGS. 2 and 3 are drawings for explaining the charge sharing. FIG. 2 is a cross-sectional view of a detecting element included in an X-ray detector 22 of a direct-conversion type serving as a comparison example. FIG. 3 illustrates the detecting element included in the X-ray detector 22 of the direct-conversion type serving as the comparison example, as viewed from the anode side. Further, although FIGS. 2 and 3 each illustrate only the two detecting elements, the X-ray detector 22 includes, in actuality, a plurality of detecting elements arranged in a two-dimensional array formation.

In the present example, similarly to the direct-conversion type detector 12 according to the present embodiments, the X-ray detector 22 is an X-ray detector of a direct-conversion type. Each of the detecting elements in the X-ray detector 22 includes: a scattered ray eliminating unit 220: a crystal (a semiconductor crystal) 221 configured to directly convert X-rays, which is radiation, into electrons; and a common electrode 222 and pixel electrodes 223 that are provided on a different one of the two faces of the crystal 221 positioned opposite from each other. The common electrode 222 corresponds to the cathode electrode and is positioned on the X-ray (radiation) incident side. The plurality of pixel electrodes 223 correspond to the plurality of anode electrodes (the electrodes from which the electrons flow out) arranged so as to oppose the cathode electrode and are positioned on the DAS 18 side. The crystal 221 is provided between the cathode electrode and the plurality of anode electrodes and is configured to directly convert the radiation into the electrons. The scattered ray eliminating unit 220 is arranged on the X-ray incident side of the common electrode 222. The scattered ray eliminating unit 220 includes a plurality of scattered ray eliminating parts (hereinafter, "ASGs") 202 arranged along the channel direction. The ASGs 202 each extend in the row direction (the Z direction), while being positioned straight above the spaces between any two adjacently-positioned pixel electrodes 223. The ASGs may each further extend in the channel direction, while being positioned straight above the spaces between any two adjacently-positioned pixel electrodes 223. In other words, the ASGs may further be arranged in a second direction different from the first direction.

In the X-ray detector 22, an electric field is generated by application of bias voltage, while the common electrode 222 and the pixel electrodes 223 are used as a cathode and an anode, respectively. Accordingly, as illustrated in FIG. 2, when an X-ray becomes incident from the common electrode 222 side and is absorbed by the semiconductor crystal 221, so that an electron-hole pair is generated, the electrons move to the pixel electrodes 223 on the anode side, whereas the electron holes move to the common electrode 222 on the cathode side.

As for the pixel electrodes 223 on the anode side, as illustrated in FIG. 3, the plurality of electrodes are arranged in a two-dimensional array formation, so that the outputs from the electrodes correspond to a pixel. In the example of the X-ray detector 22, a plurality of electrodes (nine electrodes in the drawings, which hereinafter will be referred to as "element electrodes") are arranged in the two-dimensional array formation, with respect to one detecting element 224. The number of element electrodes belonging to each of the pixel electrodes 223 does not necessarily have to be nine and may be in any quantity, as long as it is possible to avoid pile-up for each of the pixel electrodes 223. Further, the arrangement of the element electrodes belonging to each of the pixel electrodes 223 is not limited to the 3×3 formation illustrated in FIG. 3, and it is possible to use any arrangement pattern. Each of the plurality of element electrodes corresponds to an anode electrode. The output obtained by putting together the outputs from the element electrodes corresponds to one pixel. More specifically, to each of the element electrodes illustrated in FIG. 3, a reading circuit is connected. Further, the X-ray detector 22 is configured to output a result (corresponding to one pixel) obtained by putting together results of energy discrimination read from the element electrodes.

As explained above, as a result of arranging the plurality of element electrodes with respect to each of the detecting elements 224 so as to read an electric charge from each of the element electrodes, it is possible to realize a high counting rate with the X-ray detector 22. It is therefore possible to realize accurate detection, even when the irradiation is carried out with a large radiation amount.

Accordingly, in the direct-conversion type X-ray detector 22 illustrated in FIG. 3, the electrodes to read from are structured with the plurality of element electrodes, so that the electric charge is read from each of the element electrodes. In this situation, as for electron-hole pairs generated by one X-ray photon, the quantity thereof is proportional to the energy of the X-ray photon. Because the electron-hole pairs generated through various types of elementary processes by the X-ray photons and the X-ray detector 22 involve a Coulomb's interaction, the plurality of electron-hole pairs form a cloud-like spread (hereinafter, "cloud"). Depending on the energy of the X-ray photons, the cloud has the spread of approximately a few micrometers to tens of micrometers, for example. For this reason, in the situation where the ASGs 202 are designed to realize high definition in conjunction with miniaturization of the detecting elements, when an electron occurs at the crystal 221 positioned underneath or in the vicinity of an area underneath an ASG 202, the occurring electron is detected by one of the element electrodes on the anode side. For example, a cloud occurring in the vicinity of an area positioned straight underneath an ASG 202 (i.e., outside the area positioned straight underneath the ASG 202) spreads rather widely before reaching the pixel electrode 223 due to a drift diffusion of carriers of the cloud and is observed, as a result, as charge sharing. In other words, X-ray photons becoming incident at least to the outside of the areas positioned straight underneath the ASGs 202 may also be a cause of charge sharing (crosstalk). That is to say, when the group of electrons generated from the one X-ray photon becomes incident to the space between an element electrode 223a and another element electrode 223b, the group of electrons is divided, and the charge sharing occurs where the electrons are detected by two detecting elements (224 and 225) positioned adjacent to each other.

The smaller the element electrodes are, the more easily charge sharing as described above occurs. For example, charge sharing occurs more easily in a detector such as that illustrated in FIGS. 2 and 3 where multiple electrodes are arranged in a two-dimensional array formation with respect to the one detecting element 224.

Figure 4:
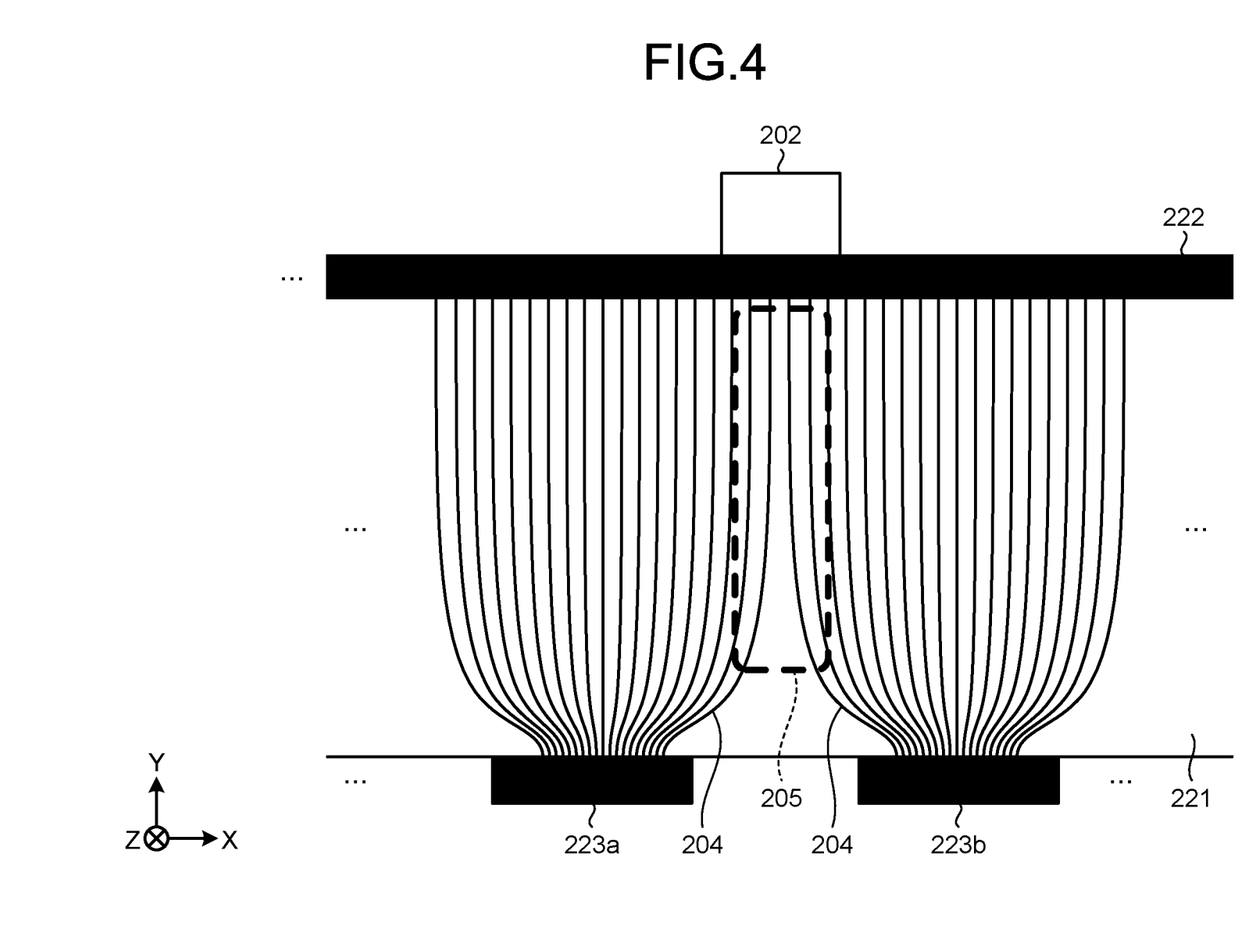
FIG. 4 is a drawing illustrating an example of lines of electric force between two element electrodes positioned adjacent to each other and a common electrode, in a direct-conversion type X-ray detector in a comparison example in FIG. 3.

FIG. 4 is a drawing illustrating an example of lines of electric force 204 between the element electrodes 223a and 223b and the common electrode 222, in the direct-conversion type X-ray detector 22 in the comparison example in FIG. 3. As illustrated in FIG. 4, for example, electrons occurring in a region 205 positioned straight underneath ASG 202 and some of the carriers caused by a drift diffusion in the cloud occurring outside the area positioned straight underneath ASG 202 are detected by either the element electrode 223a or the element electrode 223b along the lines of electric force 204. The charge sharing as described above may be a cause of crosstalk and may be a cause of noise or the like in medical images reconstructed by the reconstruction processing function 443. To solve the problem of erroneously detecting the electrons as described above, a judging circuit that judges the occurrence of charge sharing would be required.

It is an object of the direct-conversion type detector 12 according to the present embodiment to reduce crosstalk without using such a judging circuit separated by the ASGs. More specifically, the direct-conversion type detector 12 is configured to eject electrons occurring straight underneath the ASGs 202 from the direct-conversion type detector 12. A configuration of the direct-conversion type detector 12 according to the present embodiment will be explained below. The direct-conversion type detector 12 according to the present embodiment includes a conductive part that has a conductivity higher than that of the crystal 221 and is provided between the plurality of anode electrodes while being positioned straight underneath the scattered ray eliminating unit 220 including the ASGs 202. In other words, the conductive part is provided between the plurality of anode electrodes and has the conductivity higher than that of the crystal 221.

Figure 5:
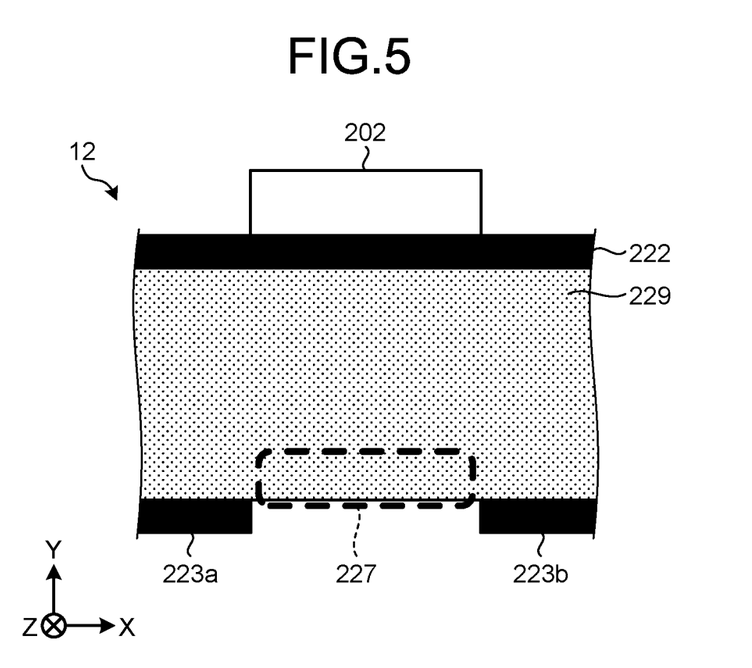
FIG. 5 is a drawing illustrating an example of an X-Y cross-section of a direct-conversion type detector according to the embodiment.

FIG. 5 is a drawing illustrating an example of an X-Y cross-section of the direct-conversion type detector 12 according to the present embodiment. The difference from FIG. 3 lies in that the direct-conversion type detector 12 includes a conductive part 227 that has a higher conductivity than that of a crystal (a semiconductor crystal) 229 and is provided between adjacently-positioned pixel electrodes 223, while being positioned in a vicinity region (hereinafter, "inter-pixel street line") of the adjacently-positioned pixel electrodes 223, which is in an area straight underneath the ASG 202. The crystal 229 in the present embodiment is provided between the cathode electrode used as the common electrode 222 and the plurality of anode electrodes used as the pixel electrodes 223 and is configured to directly convert radiation (e.g., the X-rays) into electrons.

The conductive part 227 is realized by doping (adding) impurities to the inter-pixel street line of the crystal 229 positioned on the side of the plurality of anode electrodes. As a result, defects occur in the inter-pixel street line of the crystal 229, so that the conductivity of the conductive part 227 becomes higher than that observed inside the crystal 229. In other words, because the defects are introduced, the conductive part 227 is metallized, for example, and has lower resistance than that observed inside the crystal 229. In this situation, it is possible to use any substance as the impurities, as long as the conductivity of the crystal is enhanced. In an example, the conductive part 227 may be provided in an outer circumferential part of the face of the crystal 229 where the anode electrodes are arranged. In that situation also, the conductive part 227 is provided for the crystal 229 located at the outer circumferential part, while being positioned out of contact with the pixel electrodes 223. Alternatively, the conductive part 227 may be arranged between element electrodes positioned adjacent to each other.

The impurities are added to the crystal 229 so that a conductivity $\rho$ of the conductivity part 227 becomes lower than a conductivity $C_{AE}$ of the anode electrodes ($\rho<C_{AE}$). Further, the impurities are added to the crystal 221 so that, for example, the conductivity $\rho$ of the conductivity part 227 is higher than a value obtained by multiplying a conductivity $C_c$ of the crystal by 10 ($\rho>10\times C_c$). In other words, the conductivity $\rho$ of the conductivity part 227 is higher than the value obtained by multiplying the conductivity Cc of the crystal by 10 and is lower than the conductivity $C_{AE}$ of the anode electrodes ($10\times C_c<\rho<C_{AE}$). Further, the width of the conductive part 227, i.e., the width of the inter-pixel street line, is smaller than the length of the interval between the two adjacently-positioned pixel electrodes 223. The width of the conductive part 227 may be, for example, in the range from tens of micrometers to 200 micrometers, depending on the length of the interval between the two adjacently-positioned pixel electrode 223.

The method for realizing the conductive part 227 is not limited to adding impurities to the crystal. For example, the conductive part 227 may be provided by arranging a conductor having the conductivity $\rho$ so as to be in contact with the crystal 229, while being positioned in the inter-pixel street line.

Figure 6:
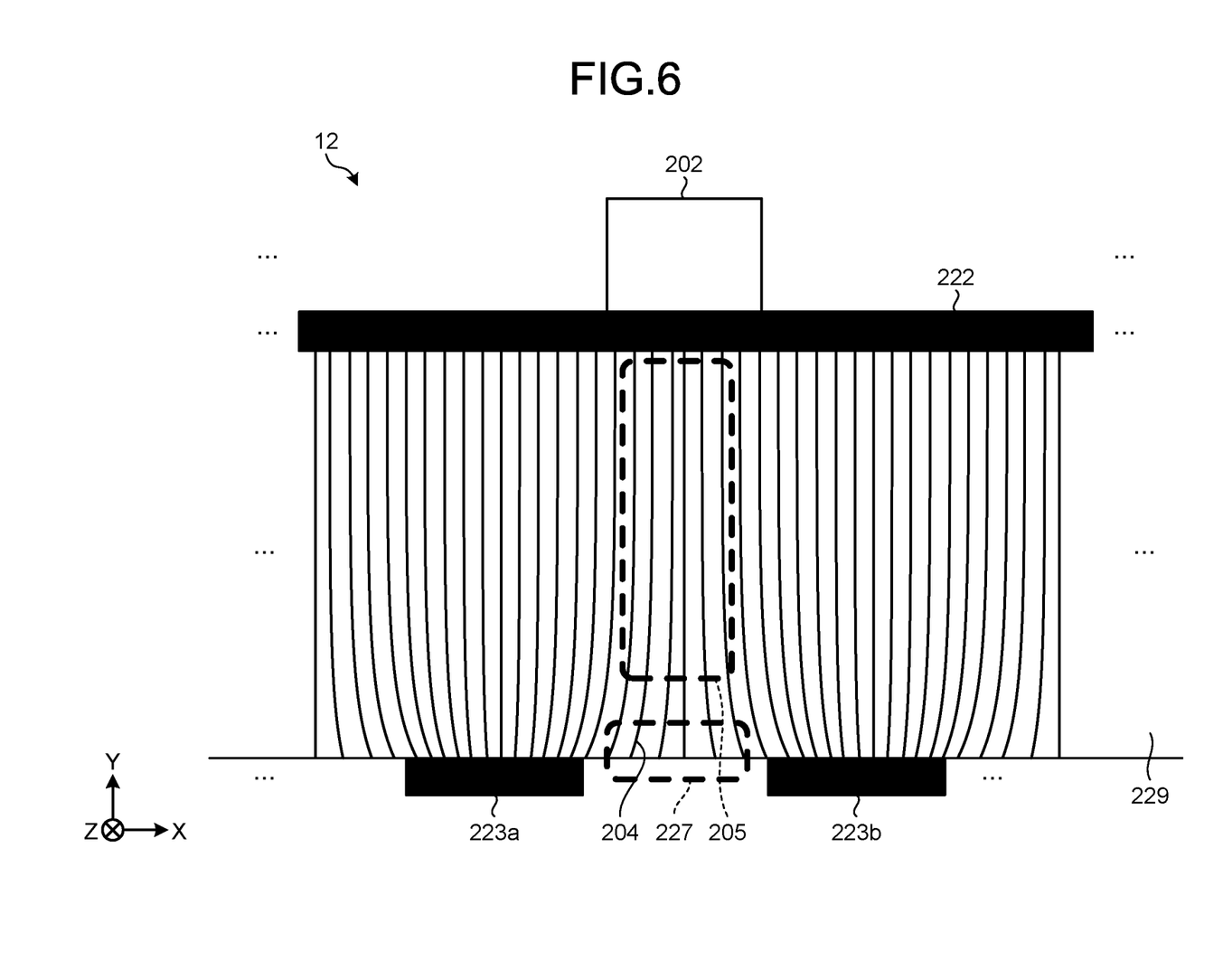
FIG. 6 is a drawing illustrating an example of lines of electric force between two element electrodes positioned adjacent to each other and a common electrode, in the direct-conversion type detector according to the embodiment.

FIG. 6 is a drawing illustrating an example of the lines of electric force 204 between the element electrodes 223a and 223b and the common electrode 222, in the direct-conversion type detector 12. As illustrated in FIG. 6, for example, electrons occurring in a region 205 positioned straight underneath the ASG 202 move along the lines of electric force 204 and are therefore not detected by the element electrode 223a or the element electrode 223b. In other words, the electrons occurring in the region 205 positioned straight underneath the ASG 202 move to the conductive part 227 provided between the element electrode 223a and the element electrode 223b.

Figure 7:
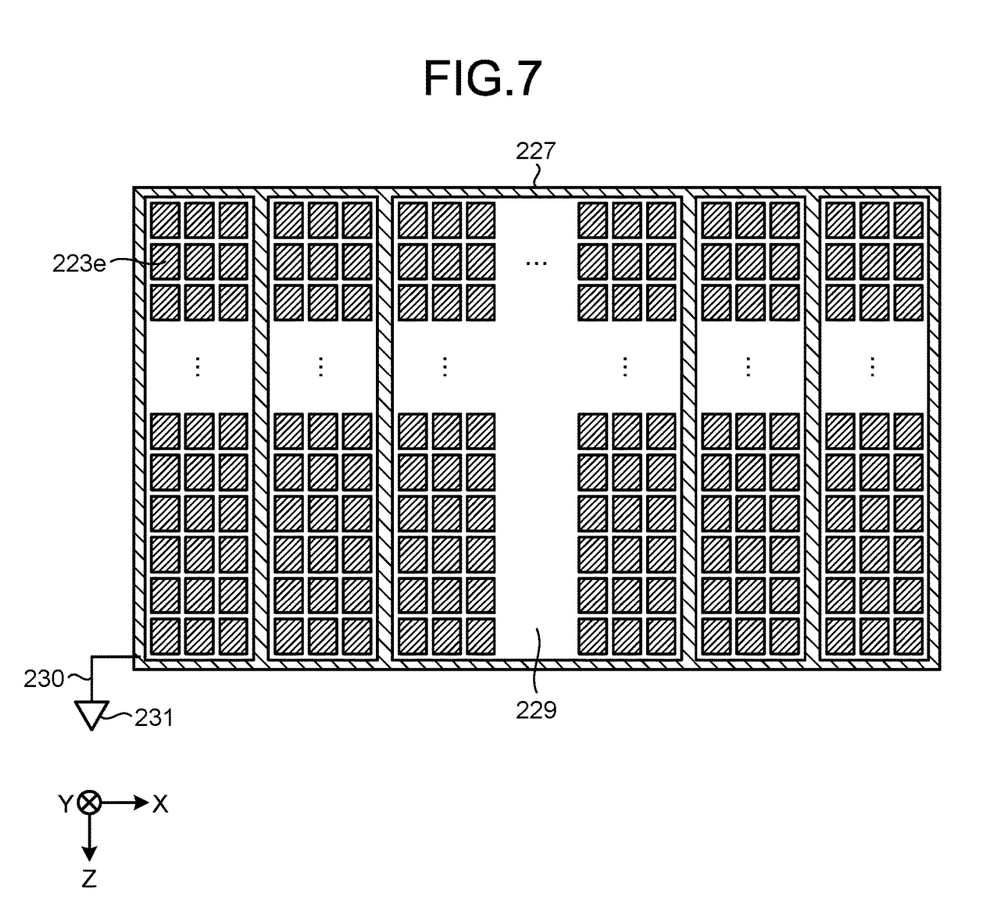
FIG. 7 is a drawing illustrating detecting elements of the direct-conversion type detector according to the present embodiment, as viewed from the side on which anode electrodes are provided.

FIG. 7 is a drawing illustrating the detecting elements of the direct-conversion type detector 12, as viewed from the side on which anode electrodes 223e are provided. As illustrated in FIG. 7, the conductive part 227 further has a ground part 231 that grounds the electric potential of the conductive part 227 to a potential reference point via a conductive path 230 that is electrically connected. The conductive path 230 corresponds to a metal wiring, for example. The ground part 231 may be called an earth or a ground. The ground part 231 is provided with respect to each of the plurality of X-ray detecting modules each including the cathode electrode 222, the plurality of anode electrodes 223e, the crystal 229, the scattered ray eliminating unit 220, and the conductive part 227. For example, the ground part 231 is configured to electrically connect a metal casing of the X-ray detection module to the conductive path 230.

The X-ray CT apparatus 1 according to the embodiment described above includes: the cathode electrode 222 provided on the X-ray incident side; the plurality of anode electrodes 223e arranged so as to oppose the cathode electrode 222; the crystal 229 provided between the cathode electrode 222 and the plurality of anode electrodes 223e and configured to directly convert the incident X-rays into the electrons; the conductive part 227 that is provided between the plurality of anode electrodes and has a conductivity higher than that of the crystal 229; the scattered ray eliminating unit 220 provided on the X-ray incident side of the cathode electrode 222 so as to oppose the conductive part 227 via the crystal 229, while being arranged in the first direction; and the image generating unit configured to generate a medical image on the basis of the electrons output from the anode electrodes 223e.

With this configuration, by using the X-ray CT apparatus 1 according to the present embodiment, it is possible to cause the electrons occurring at the crystal 229 in the region 205 positioned straight underneath the ASG 202 to move to the conductive part 227 along the lines of electric force 204, i.e., it is possible to trap the electrons. As a result, by using the X-ray CT apparatus 1 configured in this manner, it is possible to reduce charge sharing without the need to use a judging circuit configured to judge the occurrence of charge sharing. It is therefore possible to reduce crosstalk that may occur between the adjacently-positioned detecting elements (e.g., 224 and 225). Consequently, by using the X-ray CT apparatus 1 configured in this manner, even when the ASGs 202 are designed to realize high definition in conjunction with miniaturization of the detecting elements, it is possible to reduce the noise in the medical images without the need to enlarge the intervals between the pixel electrodes, while enhancing the quality of the medial images with the pixels designed to realize the high definition.

Further, in the X-ray CT apparatus 1 according to the present embodiment, the width of the conductive part 227 is arranged to be smaller than the length of the interval between any two of the anode electrodes 223e positioned adjacent to each other. Further, in the X-ray CT apparatus 1 according to the present embodiment, the conductivity of the conductive part 227 is lower than the conductivity of the anode electrodes 223e. With these arrangements, by using the X-ray CT apparatus 1, it is possible to cause the electrons occurring at the crystal 229 in the region 205 positioned straight underneath the ASG 202 to move to the conductive part 227 more restrictively, without causing the electrons occurring at the crystal 229 outside the areas positioned straight underneath the ASG 202 to move to the conductive part 227.

Further, in the X-ray CT apparatus 1 according to the present embodiment, the scattered ray eliminating unit 220 is further arranged in the second direction different from the first direction. In other words, in the X-ray CT apparatus 1, the ASGs (the scattered ray eliminating parts) 202 are each further extended in the channel direction, while being positioned straight above the space between the two anode electrodes 223e. With this arrangement, by using the X-ray CT apparatus 1, it is also possible to reduce the charge sharing in the channel direction. It is therefore possible to further reduce crosstalk that may occur between the adjacently-positioned pixel electrodes 223, i.e., crosstalk that may occur between the adjacently-positioned detecting elements.

Further, the X-ray CT apparatus 1 according to the present embodiment further includes the ground part 231 configured to ground the electric potential of the conductive part 227 to the potential reference point such as the metal casing of the X-ray detecting module, for example, via the conductive path 230 electrically connected to the conductive part 227. With this arrangement, by using the X-ray CT apparatus 1, it is possible to trap the carriers (the electrons) that have entered between the two adjacently-positioned pixel electrodes 223 and to eject the electrons to the outside of the device serving as the detecting element. As a result, it is possible to continuously trap electrons and to keep reducing the charge sharing, i.e., the crosstalk that may occur between the adjacently-positioned pixel electrodes 223.

In a modification example of the present embodiment where a technical concept of the embodiments is realized in a radiation detector, the radiation detector includes: the cathode electrode 222 provided on the radiation incident side; the plurality of anode electrodes 223e arranged so as to oppose the cathode electrode 222; the crystal 229 provided between the cathode electrode 222 and the plurality of anode electrodes 223e and configured to convert radiation into electrons; the conductive part 227 that is provided between the plurality of anode electrodes and has a conductivity higher than that of the crystal 229; and the scattered ray eliminating unit 220 provided on the radiation incident side of the cathode electrode 222 so as to oppose the conductive part 227 via the crystal 229, while being arranged in the first direction. Because advantageous effects of the present modification example are the same as those of the embodiments, the explanations thereof will be omitted.

According to at least one aspect of the embodiments described above, it is possible to reduce crosstalk that may occur between the adjacently-positioned detecting elements. Consequently, even when the intervals between the adjacently-positioned ASGs are small as a result of designing the detecting elements to realize high definition, it is possible to inhibit the crosstalk.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:
1. A radiation detector, comprising:
a cathode electrode provided on a radiation incident side;
a plurality of anode electrodes arranged so as to oppose the cathode electrode;
a crystal provided between the cathode electrode and the plurality of anode electrodes and configured to convert incident radiation into electrons;
a conductor that is provided only between the plurality of anode electrodes and has a conductivity higher than that of the crystal; and
an anti-scatter grid provided on a radiation incident side of the cathode electrode so as to oppose the conductor via the crystal, while being arranged in a first direction.

2. The radiation detector according to claim 1, wherein a width of the conductor is smaller than a length of an interval between any two of the anode electrodes positioned adjacent to each other.

3. The radiation detector according to claim 1, wherein the conductivity of the conductor is lower than a conductivity of the anode electrodes.

4. The radiation detector according to claim 1, wherein the anti-scatter grid is further arranged in a second direction different from the first direction.

5. The radiation detector according to claim 1, further comprising a ground configured to ground electric potential of the conductor to a potential reference point, via a conductive path electrically connected to the conductor.

6. The radiation detector according to claim 5, wherein the ground is provided with respect to each of a plurality of radiation detecting modules each including the cathode electrode, the plurality of anode electrodes, the crystal, the anti-scatter grid, and the conductor.

7. A radiation diagnosis apparatus, comprising:
- a cathode electrode provided on a radiation incident side;
- a plurality of anode electrodes arranged so as to oppose the cathode electrode;
- a crystal provided between the cathode electrode and the plurality of anode electrodes and configured to convert incident radiation into electrons;
- a conductor that is provided only between the plurality of anode electrodes and has a conductivity higher than that of the crystal;
- an anti-scatter grid provided on a radiation incident side of the cathode electrode so as to oppose the conductor via the crystal, while being arranged in a first direction; and
- processing circuitry configured to generate a medical image based on the electrons output from the anode electrodes.

8. A radiation detector, comprising:
- a cathode electrode provided on a radiation incident side;
- a plurality of anode electrodes arranged so as to oppose the cathode electrode;
- a crystal provided between the cathode electrode and the plurality of anode electrodes and configured to convert incident radiation into electrons;
- a conductor that is provided between the plurality of anode electrodes and has a conductivity higher than that of the crystal; and
- an anti-scatter grid provided on a radiation incident side of the cathode electrode so as to oppose the conductor via the crystal, while being arranged in a first direction,
- wherein a width of the conductor is smaller than a length of an interval between any two of the anode electrodes positioned adjacent to each other, the interval excluding any portions of the two of the anode electrodes positioned adjacent to each other.

* * * * *